(12) United States Patent
Freeman et al.

(10) Patent No.: US 7,062,110 B2
(45) Date of Patent: Jun. 13, 2006

(54) SENSOR DEVICE

(75) Inventors: Neville John Freeman, Tarporley (GB); Gerard Anthony Ronan, Salford (GB); Marcus Swann, Salford (GB); Graham Cross, Stockton-on-Tees (GB)

(73) Assignee: Farfield Sensors Limited (GB)

( * ) Notice: Subject to any disclaimer, the term of this patent is extended or adjusted under 35 U.S.C. 154(b) by 76 days.

(21) Appl. No.: 10/344,799

(22) PCT Filed: Aug. 14, 2001

(86) PCT No.: PCT/GB01/03617

§ 371 (c)(1),
(2), (4) Date: Jun. 19, 2003

(87) PCT Pub. No.: WO02/14841

PCT Pub. Date: Feb. 21, 2002

(65) Prior Publication Data

US 2004/0008919 A1    Jan. 15, 2004

(30) Foreign Application Priority Data

Aug. 14, 2000  (GB) ................... 0019889.5
Aug. 17, 2000  (GB) ................... 0020249.9

(51) Int. Cl.
    *G02B 6/00*    (2006.01)
(52) U.S. Cl. .............. 385/12; 356/477; 356/481; 356/517; 250/227.14
(58) Field of Classification Search ........... 385/12–13; 356/477, 481, 517; 250/227.14
    See application file for complete search history.

(56) References Cited

U.S. PATENT DOCUMENTS 5,120,131 A * 6/1992 Lukosz ................. 356/481
2004/0042933 A1* 3/2004 Lewis et al. ............ 422/98
2005/0122572 A1* 6/2005 Campbell et al. ...... 359/337.22

FOREIGN PATENT DOCUMENTS

GB    WO 98/22807    * 5/1988

* cited by examiner

Primary Examiner—Leonidas Boutsikaris
(74) Attorney, Agent, or Firm—Traskbritt, P.C.

(57) ABSTRACT

The present invention relates to a sensor device and method for measuring a property associated with the introduction of or changes in a chemical, biological or physical stimulus in a localized environment, in particular to a sensor device and method for measuring the partition coefficient of a chemical stimulus such as a pharmaceutical compound.

42 Claims, 3 Drawing Sheets

SENSOR DEVICE

CROSS-REFERENCE TO RELATED APPLICATIONS

This application is the national stage under 35 USC § 371 of International Patent Application PCT/GB01/03617, filed Aug. 14, 2001, which claims priority to UK Patent Application No. 0019889.5 filed Aug. 14, 2000, and U.K. Patent Application No. 0020249.9, filed Aug. 17, 2000.

BACKGROUND OF THE INVENTION

The present invention relates to a sensor device and method for measuring a property associated with the introduction of or changes in a chemical, biological or physical stimulus in a localized environment, in particular to a sensor device and method for measuring the partition coefficient of a stimulus.

BRIEF SUMMARY OF THE INVENTION

There are numerous industries in which the potential utility of a system under development can be assessed by examining the physicochemical behavior of the components of the system. However, measuring a physicochemical property of a material using conventional techniques can be both time consuming and inaccurate. In particular, properties such as the physical swelling of a material of interest (as a consequence of vapor sorption or thermal changes for example) and the partitioning of a material of interest between specific media tend to be measured quantitatively using indirect means.

By way of a specific example, the partition coefficient of a material of interest is generally determined manually which is both time consuming and expensive. Where the material of interest is a new drug compound for example, the partition coefficient is a key quantitative indicator of its potency. If a drug compound will not pass efficiently across biological membranes and through biological media, it is unlikely to be therapeutically effective. One specific parameter which is used to determine the potential for candidate materials to move through such media is the octanol-water partition coefficient (the "logP value"). The logP value is a measure of the equilibrium concentration of a given material between octanol and water. The determination of the logP value is generally carried out in accordance with the prior art as follows:

1. octanol and water (which are immiscible) are shaken vigorously for an extended period of time until the concentration of the candidate drug compound is in equilibrium between the octanol phase and the aqueous phase;
2. the two immiscible components are allowed to separate on standing;
3. aliquots of the octanol phase and the aqueous phase (separately) are withdrawn and the concentrations in each phase are determined using traditional analytical techniques such as GC, HPLC or the like; and
4. the ratio of the concentration of the candidate drug compound between the two phases provides the logP value which is used to deduce the potential solubility of the candidate drug compound in biological media.

From the above description, it will be apparent that the process of determining the logP value is lengthy. Given the increasing use of combinatorial techniques by pharmaceutical companies, there are millions of new candidate drug compounds being generated on a monthly basis. There is therefore an increasing demand for a streamlined process for determining logP values to assist the drug screening program.

A sorbtion sensor with an appropriate coating may be used to determine partition coefficients. For example, a sorbiton sensor with a hydrocarbon polymer coating (e.g., polyisobutylene) could be used in place of the manual technique described above. An aqueous solution containing the candidate drug compound could be passed directly over the sorbiton sensor and a certain amount of the candidate drug compound will be partitioned into the polymer film causing a change in the refractive index of the coating. The extent of partitioning will be determined thermodynamically and can be directly related to the logP value. Although the large surface area:volume ratio of the sorbiton sensor ensures rapid equilibration and measurement, the quantitative information is unreliable due to the multiple factors contributing to the changes on the sensor surface.

Membranes are used in a wide range of well established medical applications. The ability of a candidate membrane material to partition key components in biological fluids is a key indicator of their potential as effective membranes. In general, there is a need for a reliable and rapid means of determining partitioning behavior to aid the development of membrane materials.

Partitioning is also a key indicator in the development of new wound dressings. If certain key proteins move from a patient to a test material present in a wound dressing, the likelihood of the test material sticking to the wound or supporting deleterious material may be increased. Similarly, the partitioning of certain materials away from the area of the wound may be advantageous. Thus, the partitioning behavior of candidate materials for wound dressings is an important parameter in the industry.

A further example of partitioning behavior as a key indicator is in the food industry. The movement of both gaseous and liquid materials is of importance in determining the likely effectiveness of candidate packaging materials. In general, it is advantageous if the candidate packaging materials partition unwanted materials in preference to the food material. There is a need for a reasonable and cost effective method for determining partitioning behavior to offer the packaging technologist an insight into the development of packaging strategies and the regulator a means to determine the safety of food packaging materials.

The present invention is based on the recognition that certain sensing materials exhibit a biphasic optical response on exposure to a stimulus which is attributable to compositional and dimensional factors. More particularly, the present invention provides a sensor device exhibiting a monophasic response which may be used to measure rapidly the physicochemical behavior in a localized environment in which a sensing material is exposed to a stimulus. The sensor device uses the optical properties of a specialized architecture to exhibit improved reliability, improved signal to noise ratio (sensitivity) and robustness.

Thus, viewed from one aspect, the present invention provides a sensor device for measuring a property of interest associated with the introduction of or changes in a stimulus (e.g., a chemical, physical or biological stimulus) in a localized environment, said sensor device comprising:

a sensor component including a sensing material capable of inducing or exhibiting a measurable response to a change in the localized environment caused by the introduction of or changes in the stimulus, wherein the sensor device is arranged so as to expose to the localized environment at least a part of the sensing material and wherein the sensing material is adapted to induce or exhibit a monophasic response to the change in the localized environment caused by the introduction of or changes in the stimulus.

In a preferred embodiment, the sensing material may be applied directly onto the surface of the sensor component as a sensing layer. In this embodiment, the sensor device is arranged so as to expose to the localized environment at least a part of the sensing layer and the sensing layer is adapted to induce or exhibit a monophasic response to the change in the localized environment caused by the introduction of or changes in the stimulus. The sensing material may be applied to the surface of the sensor component by any conventional technique e.g., polymer spinning, dipping or plasma polymerization.

Preferably, the monophasic response is attributable to the dominant contribution of dimensional factors to changes in the effective refractive index of the sensing material (e.g., sensing layer).

Preferably, the monophasic response is attributable to the dominant contribution of compositional factors to changes in the effective refractive index of the sensing material (e.g., sensing layer).

In a preferred embodiment, the property of interest may be swelling of the sensing layer. In this embodiment, the sensing layer is adapted to substantially eliminate the contribution of compositional factors to the effective refractive index of the sensing material.

In a preferred embodiment, the sensor device may be used to determine a physicochemical property of the stimulus to which the sensing material is exposed (e.g., its partition coefficient or concentration). By way of example, the drug industry could utilize the sensor device of the present invention to screen candidate drug compounds for their potential to cross biological membranes. In this embodiment, the sensing layer is adapted to substantially eliminate the contribution of dimensional factors (e.g., swelling) to the effective refractive index of the sensing material.

In a particularly preferred embodiment, the sensor device may be used to determine concurrently a physicochemical property of the stimulus to which the sensing material is exposed and a property of the sensing material. In this embodiment, the sensor component includes two sensing layers, a first sensing layer is adapted to substantially eliminate the contribution of dimensional factors to the effective refractive index of the sensing material and a second sensing layer is adapted to substantially eliminate the contribution of compositional factors to the effective refractive index of the sensing material. The first and second sensing layer may (if desired) be provided on separate sensor components.

Typically the sensing layer is adapted to induce or exhibit a monophasic response by empirically selecting an appropriate thickness. For example, the film thickness of the sensing layer may be measured against phase change over a range of thicknesses to identify the specific thickness (or thicknesses) at which a monophasic response occurs.

The architecture of the sensor device of the invention may be organized in such a way as to enable precise measurements to be made either across the entire architecture or at given locations. It may be designed such as to reduce contributions from the ambient environment and unwanted 'background' events.

In the sensor device of the present invention, the method of interrogation may be evanescent field mode or whole waveguide mode. In the latter case, the sensing layer acts as a sensing waveguide and interrogation is direct.

The sensor device of the invention is preferably used in evanescent mode and comprises a secondary waveguide in which the sensing layer is capable of inducing a measurable response to a change in the localized environment caused by the introduction of or changes in the stimulus. In this embodiment, the sensor device is advantageously adapted to optimize the evanescent component so as to induce in the secondary waveguide a measurable optical response.

Generally speaking, it is known to make use of the evanescent field component of electromagnetic radiation incident on a waveguide structure (i.e., the field which extends outside the guiding region) to sense discrete changes in optical properties (see inter alia GB-A-2228082, U.S. Pat. No. 5,262,842, WO-A-97/12225 and GB-A-2307741). This method relies on "leakage" of optical signals from the waveguide structure into the sensing layer. The evanescent component of the optical signal being guided by the waveguide structure is typically small leading to limited interrogation of the sensing layer. This 'leakage' or evanescent field has well defined characteristics, rapidly decaying as the distance from the surface of the sensor platform increases.

Preferably, the sensor device in evanescent mode comprises a secondary waveguide and a reference secondary waveguide. It is preferred that the secondary waveguide and reference secondary waveguide have identical properties. Preferably, the secondary waveguide comprises silicon oxynitride or silicon nitride. The reference secondary waveguide may comprise silicon oxynitride or silicon nitride so as to have identical properties to the secondary waveguide.

Preferably, the (or each) waveguide of the sensor component is a planar waveguide (i.e., a waveguide which permits light propagation in any arbitrary direction within the plane). Preferably, the sensor component of the sensor device of the invention constitutes a multi-layered structure (e.g., a laminate structure). In this sense, the sensor device is simple to fabricate and fault tolerant in terms of construction errors. In a preferred embodiment, the plurality of layers in the sensor component are built onto a substrate (e.g., composed of silicon) through known processes such as PECVD, LPCVD, etc. Such processes are highly repeatable and lead to accurate manufacture. Intermediate transparent layers may be added (e.g., silicon dioxide) if desired. Typically the component is a multilayered structure of thickness in the range 0.2–10 microns.

The sensor device of the invention may be operated as a surface plasmon resonance sensor, attenuated total reflection sensor, total internal reflection sensor, surface acoustic wave sensor, spectrophotometric device or interferometer. For example, an interferometer similar to that described in WO-A-98/22807 and also in PCT/GB01/03348 may be used. Such a sensor device is simple to fabricate and fault tolerant in terms of construction errors.

The interaction of the stimulus with the sensing material may be a binding interaction or absorbance or any other type of physical or chemical interaction. The sensing material may be functionalized or coated as appropriate for the required sensing application. Typically the sensing material is polymeric (e.g., an absorbent polymer).

In a preferred sensor device of the invention, the sensing material comprises an absorbent material (e.g., a polymeric material such as polysiloxane or an oligomeric material such as a long chain hydrocarbon e.g., a $C_{18}$-hydrocarbon) or a bioactive material (e.g., containing antibodies, enzymes, DNA fragments, functional proteins or whole cells). The absorbent material may be capable of absorbing gases, liquids or vapors containing a chemical stimulus. The bioactive material may be appropriate for liquid or gas phase biosensing.

For measuring chemical stimuli, the sensing material may be absorbent and typically polymeric or oligomeric (e.g., a $C_{18}$-oligomer such as a $C_{18}$-hydrocarbon oligomer). The oligomer may be chemically bound to the surface of the sensor component to resist stripping or dissolving during use and may be short (e.g., $C_3$) to produce a thin sensing layer, long (e.g., $C_{18}$) to produce a thick sensing layer or very long (e.g., $C_{150}$) to produce a very thick sensing layer. The oligomer may be chosen in accordance with practices familiar to those skilled in the art to vary the absorption characteristics. For example, polyethers (such as polyethylene oxide) will absorb a wider range of chemical stimuli than a $C_{18}$-hydrocarbon oligomer.

A preferred device of the invention comprises a reference material (e.g., a reference layer). The physical, biological and chemical properties of the reference material are conveniently as similar as possible (e.g., substantially identical) to those of the sensing material (with the exception of the response to the change in the localized environment caused by the introduction of or changes in the stimulus). The reference material is either untreated or inactivated with respect to the sensing mechanism utilized in the sensing material.

Preferably the sensor component includes one or more additional sensing layers or sensing regions to enable different events at different localized environments to be detected. Each sensing layer or sensing region may be provided on the same or different sensor component (e.g., in an array). In one embodiment, the sensor device comprises a second sensing layer capable of inducing or exhibiting a measurable response to a change in the localized environment caused by the introduction of or changes in the stimulus from which measurements of the thickness of the material deposited on the sensor component may be deduced. In a further embodiment, the sensor device comprises a sensing region remote from the sensing layer which is a bare region of the secondary waveguide upon which the sensing material is deposited. The sensing region acts as a reference region by advantageously compensating for changes in the refractive index of the medium containing the stimulus to which the sensor device is subjected.

In a preferred embodiment, the sensor device comprises a second sensor component including a reference material substantially incapable of inducing or exhibiting a measurable response to a change in the localized environment caused by the introduction of or changes in the stimulus, wherein the sensor device is arranged so as to expose to the localized environment at least a part of the reference layer of the second sensor component.

The first and second sensor components may be integrated or discrete. For example, the first and second sensor components may be integrated onto a common substrate (a "back-to-back sensor"). In this embodiment, the localized environment surrounds the first and second sensor component (e.g., the sensor components may be typically immersed in a liquid or gas phase stimulus) so as to expose to the stimulus at least a part of the sensing layer of the first component and at least a part of the reference layer of the second component. Alternatively, for example, the first and second sensor components may be discretely built onto separate substrates (a "dual sensor"). In this embodiment, the localized environment constitutes a gap between the first and second sensor component which the stimulus may fill so as to expose to the stimulus at least a part of the sensing layer of the first component and at least a part of the reference layer of the second component. For example, a spacer such as a microstructure may be positioned to provide a gap between the surfaces of the first and second sensor components. In certain cases, the surface tension in a liquid phase stimulus may be sufficient to maintain the gap between the first and second sensor component. The gap is typically less than 10 microns.

The sensor device may comprise one or more means for intimately exposing to the localized environment at least a part of the sensing layer, said means being optionally integrated onto the sensor component.

The means for intimately exposing to the localized environment at least a part of the sensing layer (and any additional functionality) may be provided in a microstructure positionable on the surface of and in intimate contact with the sensor component. Preferably the microstructure comprises means for intimately exposing to the localized environment at least a part of the sensing layer in the form of one or more microchannels and/or microchambers into which chemicals may be fed (or chemical reactions may take place).

In a preferred embodiment, the means for intimately exposing to the localized environment at least a part of the sensing layer is included in a cladding layer. For example, microchannels and/or microchambers may be etched into the cladding layer. The cladding layer may perform optical functions such as preventing significant discontinuities at the boundary of the sensing layer or chemical functions such as restricting access of species to the sensing layer. The cladding layer may be integrated onto the sensor component.

Preferably, the whole of or a portion of any additional functionality may be included in the cladding layer. Additionally, the sensing layer may be incorporated in the cladding layer in the form of an absorbent material. Particularly, preferably, the whole additional functionality may be provided in the cladding layer and include devices such as for example quadrature electric field tracks or other microfluidic devices.

Electromagnetic radiation generated from a conventional source may be propagated into the sensor component in a number of ways. In the preferred embodiment, radiation is simply input via an end face of the sensor component (this is sometimes described as "an end firing procedure"). Preferably (but not essentially), the electromagnetic radiation source provides incident electromagnetic radiation having a wavelength falling within the visible range. Preferably the sensor device comprises: propagating means for propagating incident electromagnetic radiation into the sensor component. For example, one or more coupling gratings or mirrors may be used. A tapered end coupler rather than a coupling grating or mirror may be used to propagate light into the lowermost waveguide.

The incident electromagnetic radiation may be oriented (e.g., plane polarized) as desired using an appropriate polarizing means. The incident electromagnetic radiation may be focused, if desired, using a lens or similar micro-focusing means.

Using electromagnetic radiation of different frequencies (either simultaneously or sequentially) may vary the contribution of the sensor component and may further enhance the utility of the device.

Multimode excitation may provide useful additional information. For example, by comparing the outer and inner areas of the interference pattern, it may be possible to determine the extent to which any refractive index change has been induced by changes in the thickness of the outer regions and the degree to which it has been effected by physicochemical changes in the inner regions.

Thus, the sensor device comprises: first irradiating means for irradiating the sensor component with TM mode electromagnetic radiation and second irradiating means for irradiating the sensor component with TE mode electromagnetic radiation. The relative phase changes of the two modes may be used to identify and quantify the nature of the optical changes taking place in the sensing layer. For example, it may be possible to attribute changes in the effective refractive index of the sensing layer to specific changes in dimension (e.g., expansion or contraction) and/or composition. The relative phase changes of the two modes may also be used to identify such changes taking place in subsequent layers when more compact structures are employed. Conveniently, measurement of capacitance and refractive mode index of the two modes yields further information on changes occurring in the absorbent layer.

Transverse electric and transverse magnetic phase shifts may be compared sequentially or simultaneously in order to resolve effective thickness changes from changes in the intrinsic refractive index in real time on the sensor device.

Electromagnetic radiation may be modulated (amplitude, frequency or phase for example) to provide additional information on the behavior of the sensor device.

An interference pattern is generated when the electromagnetic radiation from the sensor component is coupled into free space and may be recorded in a conventional manner (see for example WO-A-98/22807). An optical response of the sensor component to changes in the localized environment may be measured from movement of the fringes in the interference pattern. For example, the phase shift of the radiation in the sensor component (e.g., induced in the secondary waveguide relative to the reference secondary waveguide) may be measured. In turn, inferences about a property of interest associated with the introduction of or changes in a chemical, biological or physical stimulus in the localized environment may be made.

The sensor device of the invention may be arranged so that changes in the refractive index of material in the localized environment effect a measurable optical response (e.g., a change in the transmission of electromagnetic radiation down the secondary waveguide in evanescent mode) which manifests itself as a phase shift. For example, changes in the refractive index of material in the localized environment might occur as a consequence of a chemical reaction. The measurable response (e.g., phase shift) exhibited or induced in the secondary waveguide may be the result of changes in dielectric properties (e.g., changes in effective refractive index) of the sensing layer which is attributable to the contribution of dimensional and/or compositional factors. By way of example, the movement of the interference pattern may be used to deduce the phase shift which takes place in the secondary waveguide (e.g., relative to the reference secondary waveguide) during the passage of electromagnetic radiation through the sensor component. The relative phase shift is directly proportional to changes occurring in the effective refractive index of the sensing layer due to the introduction of or changes in a chemical, biological or physical stimulus in a localized environment.

Movement in the interference fringes may be measured either using a single detector which measures changes in the electromagnetic radiation intensity or a plurality of such detectors which monitor the change occurring in a number of fringes or the entire interference pattern. The one or more detectors may comprise one or more photodetectors. Where more than one photodetector is used this may be arranged in an array.

In an embodiment of the sensor device, the electromagnetic radiation source and one or more detectors are integrated with the device into a single assembly.

The sensor component may be excited across its width and a two-dimensional photodiode array (or the like) may be used to effectively interrogate "strips" of the sensor device (e.g., an array sensor). This may be carried out across more than one axis simultaneously or sequentially to provide spatially resolved information relating to events on the surface of the sensor component.

The sensor components may be optionally perturbed (e.g., thermally perturbed) to enable the sensor device to be biased. This enables the precise degree of optical response (e.g., phase shift) caused by the chemical or physical stimulus to be determined.

A plurality of electromagnetic radiation detector units (e.g., in an array) and/or a plurality of electromagnetic radiation sources may be used to measure in discrete areas of the sensor component simultaneously the responses to changes in the localized environment. Alternatively, the position of the electromagnetic radiation detector and electromagnetic radiation source relative to the sensor component may be changed to provide information concerning responses in discrete areas of the sensor component. For example, discrete responses to a change in the localized environment caused by the presence of the same or different stimuli may be measured in discrete areas of the sensor component. In the first instance, concentration gradients of the same stimulus may be deduced. In the second instance, discrete responses in different regions to changes in the localized environment may be measured. For this purpose, the preferred device makes use of the versatility of the evanescent mode and comprises a plurality of separate sensing layers or regions.

Measurements may be made on a multiplicity of uniformly treated sensor components using a one dimensional (linear) photodiode array or single pinhole photodiode. For example, three separate sensor components, one bare, one surface functionalized and one coated to an appropriate thickness for monophasic response may be used.

Conveniently, electrodes positioned in contact with a surface of the sensing layer or sensing waveguide enable capacitance to be measured simultaneously. The electrodes may take the form of either parallel plates laid alongside the plurality of planar waveguides or as an interdigitated or meander system laid down on the top and bottom surfaces of the sensing waveguide or sensing layer or adjacent to it. In the case of a meander system, the metal forming the electrode is responsible for absorbing excessive amounts of light and as such the capacitance is measured on an adjacent structure which is not utilized for optical measurement.

The sensing layer may be deposited on a quartz crystal or surface acoustic microbalance. This would enable the determination of either swelling per unit mass or refractive index change per unit mass of absorbed test material.

Viewed from a further aspect, the present invention provides a method for measuring a property associated with the introduction of or changes in a chemical, biological or physical stimulus in a localized environment, said method comprising:

providing a sensor device as hereinbefore defined;

introducing or causing changes in the chemical, biological or physical stimulus in the localized environment;

irradiating the sensor component with electromagnetic radiation;

measuring the optical response of the sensor component; and relating the optical response to the property associated with the introduction of or changes in the chemical, biological or physical stimulus.

Preferably, the method of the invention comprises: measuring movements in the interference pattern; and relating the movements to the property associated with the introduction of or changes in a chemical, biological or physical stimulus.

Preferably, the method of the invention comprises: measuring a plurality of discrete responses in different regions of the sensor component.

Preferably, the method of the invention is carried out in evanescent mode. Preferably, multiple irradiation sources and/or multiple detectors are used.

Measurement ambiguity can be reduced by performing dual mode irradiation and measurement thereby further enhancing performance. Thus, in a preferred embodiment, the method of the invention comprises:

irradiating the sensor component with electromagnetic radiation in TE mode;

irradiating the sensor component with electromagnetic radiation in TM mode;

measuring the optical response of the sensor component in TE mode; and measuring the optical response of the sensor component in TM mode.

By utilizing measurements in TE and TM mode, it may be advantageously possible to deduce from the monophasic response one or more additional properties associated with the stimulus (e.g., stimulus concentration above the sensing material). The manner in which this may be carried out is described elsewhere (e.g., in WO-A-01/36946).

Viewed from an even further aspect the present invention provides the use of a sensor device according to the first aspect of the invention for (1) measuring the partition coefficient of the stimulus of interest (e.g., a drug compound) or (2) measuring swelling of the sensing material.

In the preferred use for measuring swelling of the sensing material, the sensor device is calibrated so that the contribution of dimensional factors to changes in the effective refractive index of the sensing layer predominates.

In the preferred use for measuring the partition coefficient of a stimulus of interest (e.g., a drug compound), the sensor device is calibrated so that the contribution of compositional factors to changes in the effective refractive index of the sensing layer predominates.

Viewed from still a further aspect the present invention provides a process for manufacturing a sensor device as hereinbefore defined comprising:

(A) obtaining a sensor component including a sensing material capable of inducing or exhibiting a measurable response to a change in the localized environment caused by the introduction of or changes in the stimulus;

(B) arranging the sensor component so as to expose to the localized environment at least a part of the sensing material; and (C) adapting the sensing material to induce or exhibit a monophasic response to the change in the localized environment caused by the introduction of or changes in the stimulus.

Preferably step (C) comprises:

(C1) measuring the specific thickness or thicknesses of sensing material at which a monophasic response is induced or exhibited by the sensing material in the sensor component.

Particularly preferably step (C) comprises:

measuring the thickness of the sensing layer against phase change over a range of thicknesses; and identifying the specific thickness (or thicknesses) at which a monophasic response occurs.

The sensor device of the invention may be usefully integrated into existing chromatographic analyzers (such as HPLC analyzers) for the purposes of chemical analysis.

Refractometers are currently favored for such measurements but are often found to be insensitive and temperature dependent. The sensor device of the invention offers improved sensitivity.

Viewed from a yet still even further aspect the present invention provides an analyzer (e.g., an HPJJC analyzer) comprising a chromatographic separation means and one or more sensor devices as defined hereinbefore.

In the analyzer of the invention, the sensing material (e.g., its thickness) may be adapted to induce or exhibit a monophasic response to the change in the localized environment caused by the introduction of or changes in the chemical stimulus in which the response is attributable to a dominant contribution of compositional factors to changes in the effective refractive index of the sensing material.

Typically the sensor device is employed to carry out analysis downstream of the chromatographic separation means. Such separation may be carried out in the gas or liquid phase and typically the chromatographic separation means is a suitable column. The sensor device may be connected directly to the column.

The sensing material is absorbent and typically polymeric or oligomeric (e.g., a $C_{18}$-oligomer such as a $C_{18}$-hydrocarbon oligomer). The oligomer may be chemically bound to the surface of the sensor component to resist stripping or dissolving during use and may be short (e.g., $C_3$) to produce a thin sensing layer, long (e.g., $C_{150}$) to produce a thick sensing layer or very long (e.g., $C_{150}$) to produce a very thick sensing layer. The oligomer may be chosen in accordance with practices familiar to those skilled in the art to vary the absorption characteristics. For example, polyethers (such as polyethylene oxide) will absorb a wider range of chemical stimuli than a $C_{18}$-hydrocarbon oligomer. The sensing material (e.g., sensor coating) may be chosen to give a similar response to different analytes (the so-called "Universal HPLC detector" material). The sensing material may be applied to the surface of the sensor component by any conventional technique e.g., polymer spinning, dipping or plasma polymerization.

In a preferred embodiment, the one or more sensor devices and chromatographic separation means are integrated onto a common substrate (e.g., a silicon substrate). In this embodiment, it is preferred to make use of the evanescent mode.

An embodiment of the analyzer of the invention comprises two or more sensor devices downstream of the chromatographic separation means (e.g., column). By measuring the response of the sensor component of each sensor device, it is advantageously possible to determine time dependent factors such as changes in temperature or pH.

An analyzer in which there is a plurality of sensor devices and chromatographic separation means on a common substrate may further comprise multiple fluidic pathways (e.g., microchambers and microchannels) and multiple electromagnetic radiation pathways.

The term "optical" used hereinbefore means radiation of any wavelength in the electromagnetic spectrum or the selective absence of such radiation (as in obscuration devices).

BRIEF DESCRIPTION OF THE SEVERAL VIEWS OF THE DRAWINGS

The invention will now be described in a non-limitative sense with reference to the accompanying figures in which.

Figure 2:
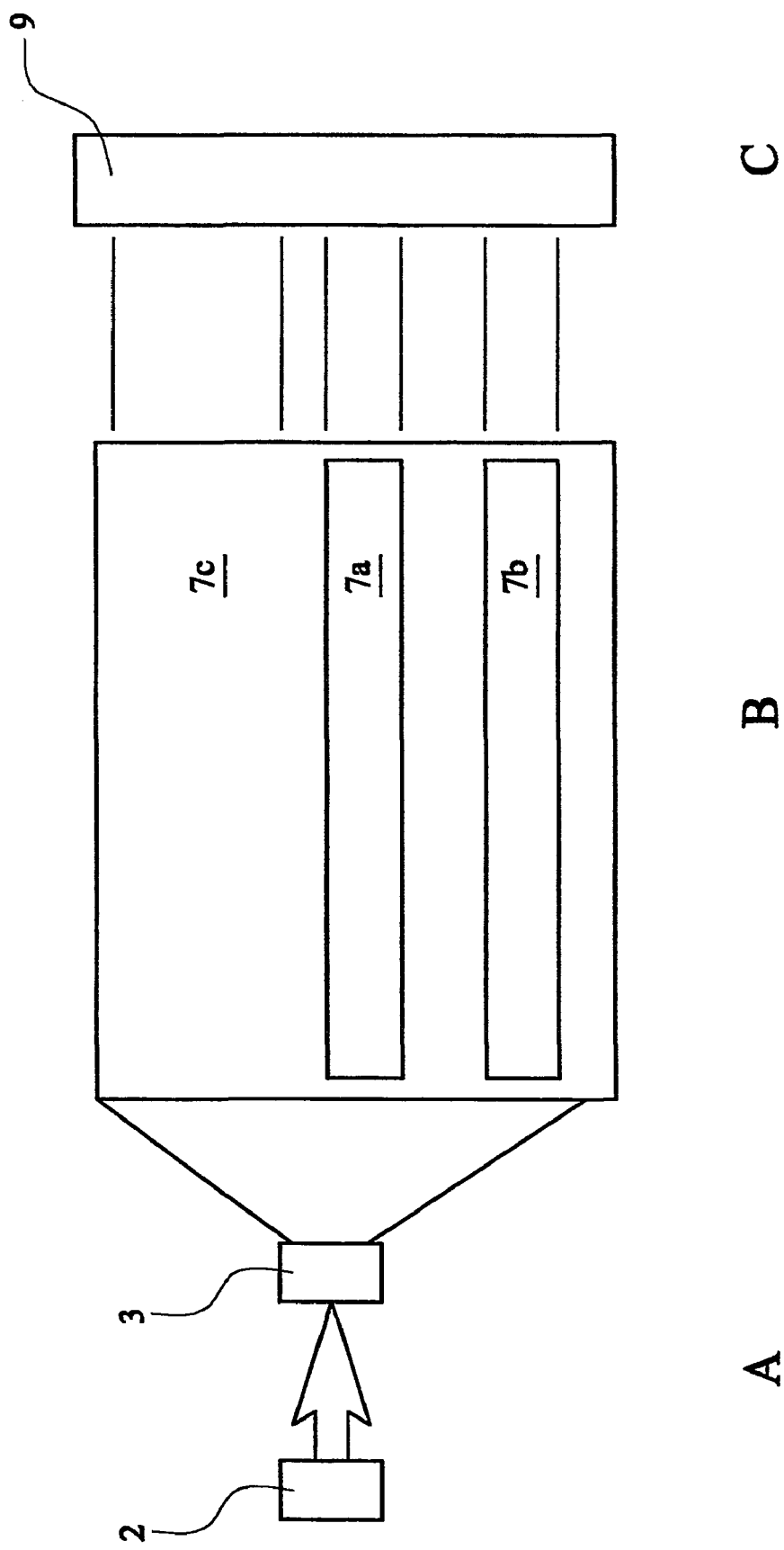
FIGS. 2 and 3 illustrate schematically an embodiment of the sensor device of the invention in plan and side view, respectively.

An embodiment of the system is shown schematically in FIG. 2. This embodiment is an evanescent waveguide interferometer which has been designed to determine simultaneously the degree of surface coverage of a test material and the degree to which certain stimuli will partition between the bulk of the test material and medium in which the stimuli is contained.

Plane polarized radiation is generated by a suitable source (not shown). The radiation is focused using a lens or micro-focusing object 2, oriented as desired using a polarizer 3 and passed to the sensor component (B). In the present embodiment the structure is fabricated from a silicon substrate 4, silicon dioxide transparent waveguides 5a and 5b, a silicon oxynitride secondary waveguide 6a, a silicon oxynitride reference secondary waveguide 6b, a first sensing layers 7a, a second sensing layer 7b and a sensing region 7c. The excitation radiation interacts with the sensing layers and sensing region whose characteristics are:

7c has no coating;

7a is a first sensing layer of test material of sufficient thickness to elicit a monophasic response from exposure to the stimuli; and 7b is a second sensing layer of test material of sufficient thickness to elicit a monophasic response from exposure to the stimuli.

Each of 7a, 7b and 7c could be provided on three separate sensors. The purpose of 7c is to act as a reference region compensating for any changes in the refractive index of the medium containing the stimulus to which the sensor is subjected. 7a provides a measure of the degree of swelling which occurs when the test material is subjected to the medium containing the stimulus and for this purpose the thickness of 7a has been calibrated so that the contribution of dimensional factors dominate the contribution of compositional factors. 7b provides a measure of the degree of partitioning of the stimulus between the test material and the medium in which the stimulus is contained and for this purpose the thickness of 7b has been calibrated so that the contribution of compositional factors dominate the contribution of dimensional factors.

The device is optimized in order to balance the amount of radiation entering the secondary waveguide 6a with that entering the reference secondary waveguide 6b. Having passed down the sensor component B, the output radiation is coupled into free space thus generating an interference pattern 8. The pattern 8 is recorded using a two dimensional photodetector array 9. The pattern is used to determine the relative phase shift induced in the secondary waveguide when compared to the reference secondary waveguide. The relative phase shift is directly proportional to changes occurring in the sensing layers 7a and 7b deposited on the surface of the secondary waveguide 6a. The sensor device provides information which is spatially resolved on the photodetector array 9 relating to both surface and bulk effects as well as using sensing region 7c to compensate for external variation in the medium of the stimulus to which the sensor device is subjected.

EXAMPLE 1

Figure 1:
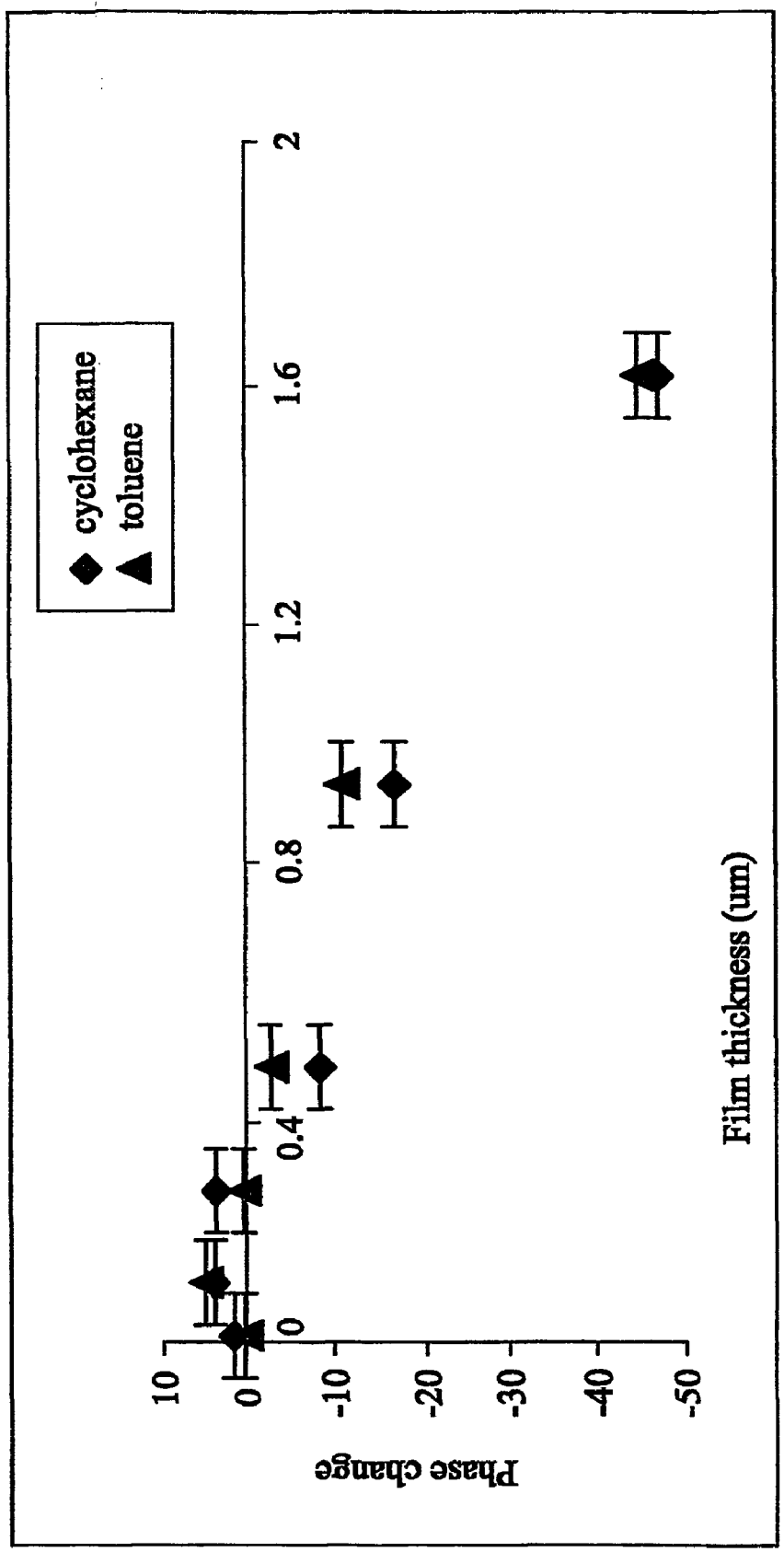
FIG. 1 illustrates phase shift data derived from an evanescent type sensor device as film thickness of the sensing layer is changed.
Figure 3:
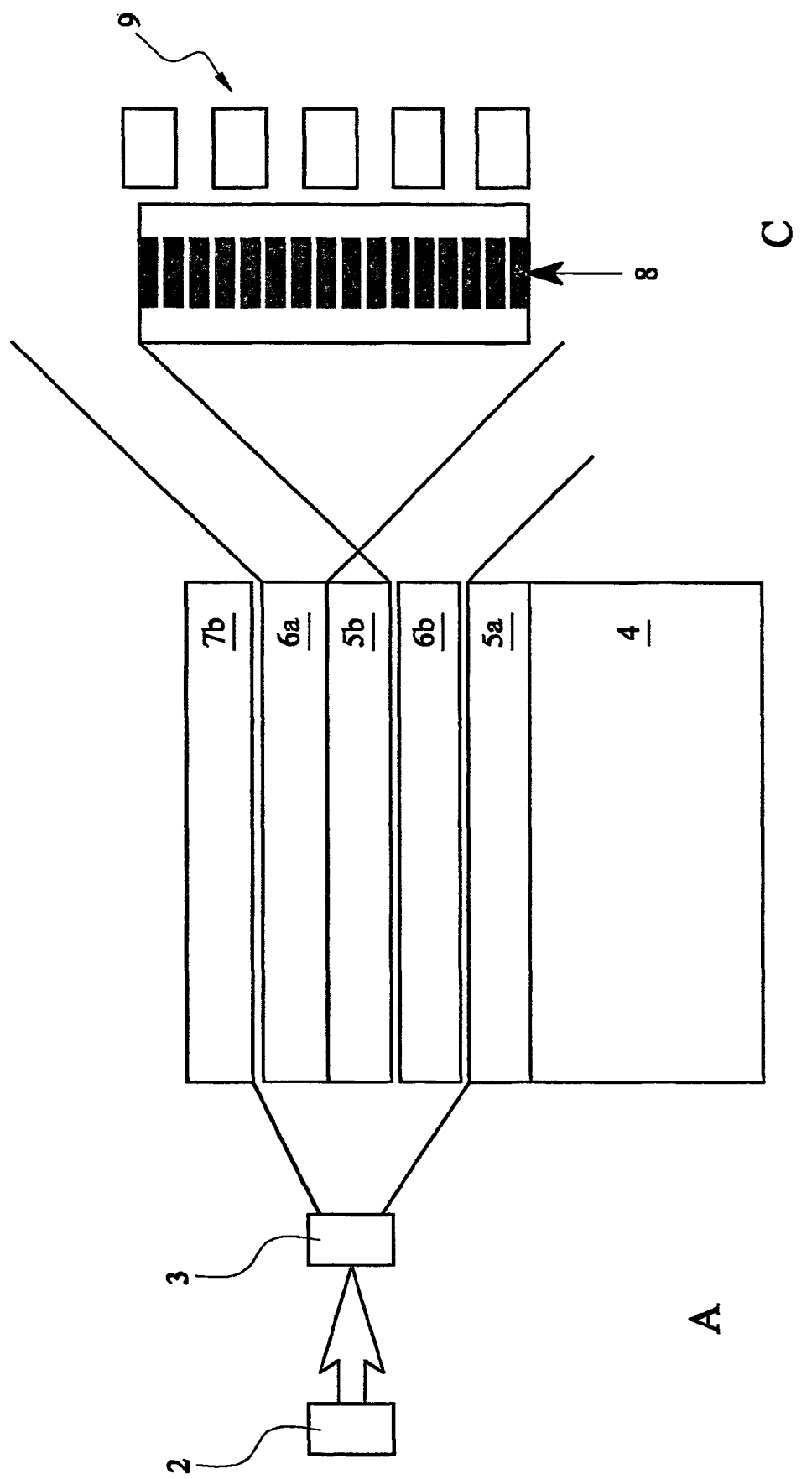

The data in FIG. 1 was derived from an evanescent wave type interferometric device of the type illustrated in FIG. 3 with a film of interest deposited on the top surface. The sensor component had the following characteristics:

| Layer | Index | Thickness (µm) |
|---|---|---|
| 5a | 1.49 | 2 |
| 6b | 1.505 ± 0.005 | 1 |
| 5b | 1.47 | 3 |
| 6a | 1.505 – 1.500 (max – min) | 1 |

The behavior of a polyisobutylene (PIB n=1.50) film of varying thickness was examined upon exposure to 50% saturated toluene (n=1.49) and cyclohexane (n=1.42) vapors.

The results are illustrated in units of relative phase change versus film thickness. The increase in film thickness upon swelling dominates the response of the ultra-thin region of the film. In the thin film limit, in spite of the fact that the refractive indices of both toluene and cyclohexane are lower than that of PIB, a relative phase increase is seen. This relates to an increase in effective refractive index. The increase in the film thickness due to swelling dominates the decrease in the bulk film refractive index in this thickness regime. With thicker films, the negative compositional refractive index change becomes apparent. In thicker regimes, the thickness increase effect becomes negligible and the relative phase decrease is dominated by the bulk decrease in refractive index.

SUMMARY

There are essentially two factors contributing to changes in the effective refractive index of the film so that at most thicknesses the response of the sensor device is a biphasic response. Only at certain film thickness will one or other of the contributory factors predominate so that a monophasic response is elicited from the sensor device. The film thickness providing the monophasic response depends on the test material and may be determined empirically. In Example 1, a thickness typically greater than 1.6 µm exhibits a monophasic response when the contribution of the compositional factors dominate the contribution of the dimensional factors.

EXAMPLE 2

The method described in Example 1 for distinguishing dimensional effects from compositional effects is crucial for elucidating important parameters to allow measurement of (for example) partition coefficients. In particular, it is important to note that if the thickness is not chosen correctly a zero phase response will be seen, leading to incorrect assumptions about the partitioning behavior of the test material.

By way of example, the following steps set out schematically how new chemical (e.g., drug) compounds may be rapidly screened by a chemical company to determine their partition coefficient:

(1) select a polymer to coat the surface of a sensor device of the type described hereinbefore;

(2) calibrate the polymer coating using a series of standards to determine the optical response at different thicknesses;

(3) select a thickness which induces a monphasic response (see Example 1);

(4) coat a sensor device of the type described hereinbefore with the polymer at the selected thickness;

(5) fit the sensor device to ancillary instrumentation to create a sensor assembly;

(6) supply the sensor assembly to the chemical company;

(7) the chemical company recalibrates the sensor device; and (8) the chemical company runs a series of samples and the response of each is compared to a standard to determine the logP coefficient.

The invention claimed is:

1. A sensor device for measuring a property of interest comprising a partition coefficient of a physicochemical property associated with an introduction of or changes in a stimulus in a localized environment, said sensor device comprising:
a sensor component including a sensing material capable of inducing or exhibiting a measurable response to a change in the localized environment caused by the introduction of or changes in the stimulus, wherein the sensor device is arranged so as to expose to the localized environment at least a part of the sensing material and wherein the sensing material is adapted to induce or exhibit a monophasic response to the change in the localized environment caused by the introduction of or changes in the stimulus and to substantially eliminate a contribution of dimensional factors to changes in an effective refractive index thereof.

2. A sensor device as claimed in claim 1 wherein the stimulus is a chemical stimulus.

3. A sensor device as claimed in claim 1 wherein the sensing material is applied directly on the surface of the sensor component as a sensing layer and the thickness of the layer is adapted to induce or exhibit a monophasic response to the change in the localized environment caused by the introduction of or changes in the stimulus.

4. A sensor device as claimed in claim 1 wherein the monophasic response is attributable to a dominant contribution of compositional factors to changes in the effective refractive index of the sensing material.

5. A sensor device as claimed in claim 1 wherein the property of interest is swelling of the sensing material, and the sensing material is adapted to substantially eliminate the contribution of compositional factors to changes in the effective refractive index of the sensing material.

6. A sensor device as claimed in claim 1 wherein the stimulus is a pharmaceutically active compound or a composition containing a pharmaceutically active compound, and the sensing material is adapted to substantially eliminate the contribution of dimensional factors to changes in the effective refractive index of the sensing material.

7. A sensor device as claimed in claim 1 wherein the sensing material is in the form of one or more sensing layers capable of inducing in a secondary waveguide a measurable response to a change in the localized environment caused by the introduction of or changes in the stimulus.

8. A sensor device as claimed in claim 7 wherein the secondary waveguide comprises silicon oxynitride or silicon nitride.

9. A sensor device as claimed in claim 7 further comprising an inactive secondary waveguide in which the sensing layer is incapable of inducing a measurable response to a change in the localized environment caused by the introduction of or changes in the stimulus.

10. A sensor device as claimed in claim 9 wherein the properties of the secondary waveguide and inactive secondary waveguide are essentially identical with the exception of the response to a change in the localized environment caused by the introduction of or changes in the stimulus.

11. A sensor device as claimed in claim 9 wherein the secondary waveguide and inactive secondary waveguide comprise silicon oxynitride.

12. A sensor device as claimed in claim 1 wherein the sensing material is in the form of a sensing waveguide capable of exhibiting a measurable response to a change in the localized environment caused by the introduction of or changes in the stimulus.

13. A sensor device as claimed in claim 12 further comprising an inactive waveguide substantially incapable of exhibiting a measurable response to a change in the localized environment caused by the introduction of or changes in the stimulus.

14. A sensor device as claimed in claim 13 wherein the properties of the sensing waveguide and inactive waveguide are essentially identical with the exception of the response to a change in the localized environment caused by the introduction of or changes in the stimulus.

15. A sensor device as claimed in claim 13 wherein the inactive waveguide comprises silicon oxynitride.

16. A sensor device as claimed in claim 1 wherein the sensing material is an absorbent material or a bioactive material.

17. A sensor device as claimed in claim 13 wherein each of the waveguides of the sensor component is a planar waveguide.

18. A sensor device as claimed in claim 1 wherein the sensor component constitutes a multi-layered structure.

19. A sensor device as claimed in claim 18 wherein the sensor component constitutes a laminate structure.

20. A sensor device as claimed in claim 18 wherein the multi-layered structure of the sensor component is fabricated onto a silicon substrate and consists essentially of a first absorbent layer capable of acting as a sensing layer located above and in intimate contact with a first silicon oxynitride layer capable of acting as a secondary waveguide, wherein said first absorbent layer is of a thickness such that the contribution of dimensional factors dominate the contribution of compositional factors to changes in the effective refractive index of the sensing material.

21. A sensor device as claimed in claim 18 wherein the multi-layered structure of the sensor component is fabricated onto a silicon substrate and consists essentially of a first absorbent layer capable of acting as a sensing layer located above and in intimate contact with a first silicon oxynitride layer capable of acting as a secondary waveguide, wherein said first absorbent layer is of a thickness such that the contribution of compositional factors dominate the contribution of dimensional factors to changes in the effective refractive index of the sensing material.

22. A sensor device as claimed in claim 18 wherein the multi-layered structure of the sensor component is fabricated onto a silicon substrate and consists essentially of a first absorbent layer and a second absorbent layer, each of said first and second absorbent layer being capable of acting as a sensing layer and being located above and in intimate contact with a first silicon oxynitride layer capable of acting as a secondary waveguide, wherein said first absorbent layer is of a thickness such that the contribution of compositional factors dominate the contribution of dimensional factors to the effective refractive index of the sensing material and wherein said second absorbent layer is of a thickness such that the contribution of dimensional factors dominate the contribution of compositional factors to changes in the effective refractive index of the sensing material.

23. A sensor device as claimed in claim 18 wherein a first silicon oxynitride layer is located above and spaced apart from a second silicon oxynitride layer capable of acting as a reference secondary waveguide by an intermediate silicon dioxide layer.

24. A method for measuring a property associated with the introduction of or changes in a chemical, biological or physical stimulus in a localized environment, said method comprising:
   providing a sensor device as defined in claim 1;
   introducing or causing changes in the chemical, biological or physical stimulus in the localized environment;
   irradiating the sensor component with electromagnetic radiation;
   measuring the response of the sensor component; and
   relating the response to the property associated with the introduction of or changes in the chemical, biological or physical stimulus.

25. A method as claimed in claim 24 wherein the property of interest is swelling of the sensing material.

26. A method as claimed in claim 24 wherein the response of the sensor component is movements in an interference pattern.

27. A method as claimed in claim 26 further comprising:
   calculating the phase shift from the movements in the interference pattern; and
   relating the phase shift to the property associated with the introduction of or changes in the chemical, biological or physical stimulus.

28. A process for manufacturing a sensor device as defined in claim 1 comprising:
   obtaining a sensor component including a sensing material capable of inducing or exhibiting a measurable response to a change in the localized environment caused by the introduction of or changes in the stimulus;
   arranging the sensor component so as to expose to the localized environment at least a part of the sensing material; and
   adapting the sensing material to induce or exhibit a monophasic response to the change in the localized environment caused by the introduction of or changes in the stimulus.

29. A process as claimed in claim 28 wherein comprises measuring the specific thickness or thicknesses of sensing material at which a monophasic response is induced or exhibited by the sensing material in the sensor component.

30. A process as claimed in claim 28 wherein comprises:
   measuring the thickness of the sensing layer against phase change over a range of thicknesses; and
   identifying at least one specific thickness at which a monophasic response occurs.

31. A method for determining the partition coefficient of a pharmaceutical compound, said method comprising:
   providing a first sensor device as defined in claim 1, wherein said sensing material is a polymer coating;
   measuring the response of the polymer coating at a range of thicknesses;
   selecting a specific thickness at which a monophasic response is exhibited or induced by the polymer coating;
   coating a second sensor device as defined in claim 1 with a polymer coating at the specific thickness;
   measuring the response of the second sensor device to the pharmaceutical compound;
   measuring the responses of the second sensor device to a series of samples of known partition coefficient;
   comparing the response of with the responses of the second sensor device to the series of samples of known partition coefficient; and
   determining the partition coefficient.

32. An analyser comprising a chromatographic separation means and one or more sensor devices as defined in claim 1.

33. An analyser as claimed in claim 32 comprising two or more sensor devices downstream from a chromatographic separation means, said chromatographic separation means comprising a column.

34. An analyser as claimed in claim 32 wherein the chromatographic separation means is a high performance liquid chromatographic separation means.

35. A sensor device for measuring a property of interest associated with an introduction of or changes in a stimulus in a localized environment, said sensor device comprising:
   a sensor component including a sensing material capable of inducing or exhibiting a measurable response to a change in the localized environment caused by the introduction of or changes in the stimulus, wherein the sensor device is arranged so as to expose to the localized environment at least a part of the sensing material and wherein the sensing material is adapted to induce or exhibit a monophasic response to the change in the localized environment caused by the introduction of or changes in the stimulus and the sensing material is in the form of one or more sensing layers capable of inducing in a secondary waveguide a measurable response to a change in the localized environment caused by the introduction of or changes in the stimulus.

36. The sensor device of claim 35, wherein the secondary waveguide comprises silicon oxynitride or silicon nitride.

37. The sensor device of claim 35, further comprising an inactive secondary waveguide comprising a sensing layer that is incapable of inducing a measurable response to a change in the localized environment caused by the introduction of or changes in the stimulus.

38. The sensor device of claim 37, wherein the secondary waveguide and inactive secondary waveguide have properties that are essentially identical with the exception of the response to a change in the localized environment caused by the introduction of or changes in the stimulus.

39. The sensor device of claim 37, wherein the secondary waveguide and inactive secondary waveguide comprise silicon oxynitride.

40. A method for measuring a partition coefficient of a physicochemical property of a stimulus that is associated with the introduction of or changes in a chemical, biological or physical stimulus in a localized environment, said method comprising:
   providing a sensor device comprising a sensor component including a sensing material capable of inducing or exhibiting a measurable response to a change in the localized environment caused by the introduction of or changes in the stimulus, wherein the sensor device is arranged so as to expose to the localized environment at least a part of the sensing material and wherein the sensing material is adapted to induce or exhibit a monophasic response to the change in the localized environment caused by the introduction of or changes in the stimulus;

introducing or causing changes in the chemical, biological or physical stimulus in the localized environment;

irradiating the sensor component with electromagnetic radiation;

measuring the response of the sensor component; and relating the response to the partition coefficient of the physicochemical property associated with the introduction of or changes in the chemical, biological or physical stimulus.

41. The method according to claim 40, wherein the response of the sensor component comprises at least one movement in an interference pattern.

42. The method according to claim 41, further comprising:
calculating the phase shift from the at least one movement in the interference pattern; and
relating the phase shift to the property associated with the introduction of or changes in the chemical, biological or physical stimulus.

* * * * *